United States Patent [19]

Mann et al.

[11] Patent Number: 5,085,655
[45] Date of Patent: Feb. 4, 1992

[54] COHESIVE TAPE SYSTEM

[75] Inventors: Roger H. Mann, Carona Del Mar; Karl Joseph, Los Angeles, both of Calif.; Gary A. Avalon, Painesville, Ohio

[73] Assignee: Avery Dennison Corporation, Pasadena, Calif.

[21] Appl. No.: 555,297

[22] Filed: Jul. 19, 1990

[51] Int. Cl.$^5$ ............ A61F 13/58; A61F 13/60; A61F 13/66; B32B 7/12
[52] U.S. Cl. .................. 604/389; 604/390; 428/355; 428/343
[58] Field of Search ............ 604/389, 390; 428/355, 428/343

[56] References Cited

U.S. PATENT DOCUMENTS

| | | | |
|---|---|---|---|
| 4,300,562 | 11/1981 | Pieniak | 604/389 X |
| 4,710,190 | 12/1987 | Wood et al. | 604/390 X |
| 4,759,754 | 7/1988 | Korpman | 604/389 X |
| 4,787,897 | 11/1988 | Torimae et al. | 604/389 |
| 4,791,024 | 12/1988 | Clerici et al. | 428/496 X |
| 4,810,574 | 3/1989 | Ahner | 604/390 X |
| 4,861,635 | 8/1989 | Carpenter et al. | 604/390 |

OTHER PUBLICATIONS

Japanese Abstract 87JP-296409.

Primary Examiner—George F. Lesmes
Assistant Examiner—D. R. Zirker
Attorney, Agent, or Firm—Pearne, Gordon, McCoy & Granger

[57] ABSTRACT

Thermoplastic elastomers provide autoadhesive properties at room temperature having improved anti-blocking properties. The elastomers are substantially non-adhesive. The elastomers include physical cross-links which enable the elastomers to be formed as laminates with other polymeric materials by processing techniques involving application of heat.

10 Claims, 1 Drawing Sheet

COHESIVE TAPE SYSTEM

BACKGROUND OF THE INVENTION AND RELATED ART

The present invention relates to polymeric materials useful in mounting systems and tapes for joining elements, and more particularly, to laminates and methods of making laminates including layers or films of polymeric materials having mutual adhesive properties which enable repeated fastening and separating of elements. The present invention also relates to diaper fastening systems using such polymeric materials, laminates and tapes.

The terms "autoadhesive" and "autoadhesion" are used herein to indicate the self-adhesive or cohesive-adhesive properties of a polymeric material which enable films, layers or coatings thereof to be repeatedly adhered together by application of pressure at service or room temperature and separated. Such materials are also substantially non-adhesive with respect to many other materials. Service temperature is used herein in accordance with its ordinary meaning to indicate the intended temperature or temperature range of use for the autoadhesive by the end user.

Japanese patent, application SHO62-296409, dated Nov. 25, 1987, discloses a self-adhering composition comprising a styrene-ethylene-butylene-styrene (SEBS) block copolymer and a tackifier. The tackifier is present in an amount ranging from 15 to 60 parts by weight per 100 parts by weight of SEBS block copolymer. Disclosed tackifiers include polyterpene resins, terpene phenolic resins, cyclo-aliphatic saturated hydrocarbon resins, $C_5$ and $C_9$ petroleum resins and rosin materials. If less than 15 parts of tackifier are used, it is indicated that the autoadhesion is low. On the other hand, use of more than 60 parts of tackifier is indicated to yield increased adhesive strength and adhesion to other materials. Further, the adhesion strength increases with time.

Japanese patent application SHO60-207682, dated Sept. 18, 1985, discloses an SEBS block copolymer used with or without a tackifier to provide a pressure-sensitive adhesive for use in a dust control mat. The compositions of this patent are indicated in the above-noted Japanese patent application SHO62-296409 to lack autoadhesion properties or to yield an excessively soft elastomer.

U.S. Pat. No. 4,791,024 discloses elastomers of natural rubber or a blend of natural rubber and a synthetic rubber, such as butadiene-styrene rubber, having cohesive-adhesive properties. The patent teaches that curing and cross-linking of the elastomer should be limited to retain adhesive properties. The cohesive-adhesive elastomer is itself secured to an element or article by mechanical attachment such as stapling or by cementing with a solvent solution of natural rubber. Application of the elastomer to a cotton fabric or polyvinylchloride film carrier to make a tape is disclosed. To facilitate repeated separation, the patent also teaches the use of filler materials such as threads, gauzes or powders at the exposed surface.

U.S. Pat. Nos. 4,040,124 and 3,921,221 disclose cohesive-adhesive materials derived from aqueous dispersions or solvent solutions of natural rubber or synthetic rubber for use in closures for hospital gowns. These materials are indicated to be capable of adhering to or having an affinity for bonding only to themselves. Repeated sealing and separating of the closures as well as freedom from contamination are also disclosed. U.S. Pat. No. 3,574,864 teaches the use of an aqueous natural rubber latex with casein and tackifying resins to provide similar type closures for hospital gowns.

U.S. Pat. Nos. 4,042,732 and 3,937,683 teach the use of cohesive compositions which may be sealed by manual pressing in packaging applications. The compositions comprise aqueous dispersions of natural or synthetic rubber and polyalkylmethacrylate together with an inert particulate material. Styrene-butadiene rubber and carboxylated styrene-butadiene rubber are disclosed as useful synthetic rubbers. The patent discloses application of the cohesive compositions by conventional coating methods, e.g. gravure rollers, flexographic plates or air-knife doctoring techniques. Examples of suitable wrapping materials are plastic film, such as low and high density polyethylene and polypropylene films, cellulose film or paper.

U.S. Pat. No. 3,196,034 also discloses a cohesive-adhesive composition of natural rubber or styrene-butadiene rubber for use in tape for securing film on a reel.

Ethylene-propylene rubber and ethylene-propylene-diene rubber require the use of tackifiers to achieve tackiness and green strength in accordance with U.S. Pat. No. 3,402,140 and 3,536,653. Illustrative tackifiers include phenolic resins, coumarone-indene resins, terpene resins, butadiene-styrene resins, polybutadiene resins and hydrocarbon resins. Ethylene-propylene and ethylene-propylene-diene elastomers have been used in self-fusing tape applications upon incorporation of suitable resins such as glycerol esters of hydrogenated rosin, thermoplastic terpene resins, petroleum hydrocarbon resins and others as taught in U.S. Pat. Nos. 3,470,127, 3,684,644 and 4,071,652.

The type of diaper fastening system of particular interest herein is generally illustrated in U.S. Pat. No. 4,710,190 wherein pressure-sensitive adhesives are used with a reinforcing tape on an outer liquid-impermeable layer of a diaper to provide a "landing zone" to releasably receive the diaper fastening tabs when the diaper is fastened closed. Reinforcing tape is required because the outer liquid-impermeable layer is relatively fragile and easily torn or damaged. In such systems, one of the terminal ends of each tab and the reinforcing tape are affixed to the diaper at a "factory-joint" by the diaper manufacturer using adhesives or other means. The other terminal ends of the tabs are movable by the end user from a storage and transport position to a deployed position secured to the landing zone in a "user-joint." To that end, the tab or at least the deployable end thereof is provided with a pressure-sensitive adhesive.

An inherent problem in the foregoing diaper fastening systems using pressure-sensitive adhesive tabs is that of contamination of the surfaces of the user-joint. Dust, powder, greasy or oily residues and other foreign matter on either of the two surfaces which interface at the user-joint tends to limit its strength.

SUMMARY OF THE INVENTION

It has now been discovered that certain polymeric materials comprising thermoplastic elastomers having molecules including unique combinations of monomer units and sequential arrangements thereof enable autoadhesive properties of improved stability. The elastomers are substantially non-adhesive with respect to other materials. These elastomers also afford unique processing advantages which permit them to be formed as laminates with other polymeric materials having preselected properties.

In accordance with the invention, laminates including integrally joined layers of a thermoplastic material and a thermoplastic elastomer material having autoadhesive properties at room temperature are provided. The elastomeric layer has improved anti-blocking properties which tend to reduce increases in autoadhesion with time. The elastomeric layer is substantially non-adhesive at room temperature with respect to the thermoplastic layer.

The laminates may be used to provide tape products having an autoadhesive layer formed by the layer of thermoplastic elastomer and a base or carrier layer formed by the layer of thermoplastic. Such tape products may be manufactured in the form of a web or roll stock using conventional techniques.

The laminates of the present invention are useful in diaper fastening systems, and particularly in systems of the type including a reinforcing tape which provides a landing zone. The laminates may be used to provide both fastening tabs and reinforcing tapes including the landing zones. The laminates may be secured to the diaper at a factory-joint using thermal bonding, adhesives and other techniques. The diaper fastening tab may be releasably secured at a user-joint to the landing zone of the reinforcing tape using the autoadhesive properties of the disclosed elastomers. The non-adhesive properties of the elastomers of the invention eliminate or reduce the contamination problems of the prior art systems.

The thermoplastic elastomers of the invention display increased autoadhesive stability during use since the elastomers contain physical cross-links believed to restrict the elastomer mobility and flow characteristics which contribute to the development of autoadhesive properties. Especially stable autoadhesive properties have been observed in temporary or short term applications wherein the end use of the autoadhesive joint may last no longer than one or several hours and usually less than about a day.

The thermoplastic elastomers are characterized by physical cross-links which are labile and therefore may be rendered ineffective by processing techniques involving the application of heat. In this manner, the laminates may be formed by conventional processing techniques such as coextrusion. The thermoplastic and elastomeric layers are integrally joined during such processing by heat bonding or welding at the adjacent surfaces. If necessary, an elastomeric tie layer may be used in connection with thermoplastics which are highly polar or otherwise do not tend to adhere to the elastomeric layer.

Thermoplastic elastomers of interest herein include any block copolymer having or containing the triblock structure A-B-A where A represents a block which is non-rubbery or glassy or crystalline at service or room temperature but fluid at higher temperatures, and B represents a block which is rubbery or elastomeric at service or room temperature. In addition to the A-B-A triblock structure, other possible structures include radial structures $(A-B)_n$, diblock structures A-B and combinations of these structures. The elastomer may comprise from about 60 to about 95% rubbery segments by weight and from about 5 to about 40% non-rubbery segments by weight.

The block copolymers of the elastomer form a two-phase system with the rubbery and non-rubbery segments being thermodynamically incompatible at service or room temperature. In accordance with the "domain theory", the non-rubbery segments tend to agglomerate and form hard domains which act as strong, multifunctional junction points within the elastomer matrix so that the polymer molecules behave as if joined in a cross-linked network.

The physical cross-links of the thermoplastic elastomers provide it with properties similar to those of a vulcanized rubber at room temperature. However, heating causes the domains to soften and the network to lose its strength so that the polymer may flow with application of shear force. Upon removal of heat, the original elastomer properties are regained.

Coextrusion enables unique structural arrangments and laminates of polymeric materials in accordance with the invention. In such processing, the elastomer is heated to a temperature above the glass transition temperature of the non-rubbery segment to enable polymer flow and formation of the laminate. The thermoplastic is heated to a temperature above its melt temperature during the coextrusion process, and the layers are joined by heat bonding or welding during extrusion to form the laminate as an integral, coextensive extrudate.

The physical cross-links are believed to suppress increases in long term autoadhesion by tending to limit molecular movement at the interface of cohered elastomer layers so that less interdiffusion occurs. The reduction of increases in mutual adherence and bonding, such as may occur otherwise during periods of uninterrupted joining or mounting of elements, enables the laminates to be used in mechanical-like attachments such as provided by hook and loop fasteners. Further, separating and rejoining elastomer layers of a joint tends to reduce any increase in long term autoadhesive strength.

The thermoplastic elastomers of the invention are free of tackifiers which may tend to migrate and cause damage to other laminate layers and/or alter autoadhesion properties. Also, tackifiers tend to lower the viscosity of the elastomer at elevated temperatures so as to inhibit coextrusion processing.

The thermoplastic materials useful for forming the cojoined layer include meltable film-forming thermoplastics which substantially do not adhere to the thermoplastic elastomer material at room or service temperature. Preferably, the thermoplastic should have a melt temperature sufficiently close to that of the thermoplastic elastomer to enable coextrusion of the materials and formation of a permanent melt bond therebetween, with or without the use of a tie coat, which is retained after cooling. In practice, any thermoplastic material may be used which is capable of being formed into a self-supporting continuous sheet or film having adequate mechanical properties to withstand normal handling and to fulfill the requirements of the end use application including satisfactory bonding with the thermoplastic elastomer at an elevated temperature. Suitable thermoplastic materials include various hydrocarbon polymers such as polyolefins, polyesters, polyamides, polyurethanes, polycarbonates, acrylics, cellulosics, halocarbons, ionomers, vinyls and other polymers, and their blends, interpolymers and copolymers. Preferred thermoplastic materials include polyolefins and polyesters.

BRIEF DESCRIPTION OF THE DRAWINGS

In the drawings, all of which are highly diagrammatic and do not show various elements to scale.

DETAILED DESCRIPTION OF THE DRAWINGS

Figure 1:
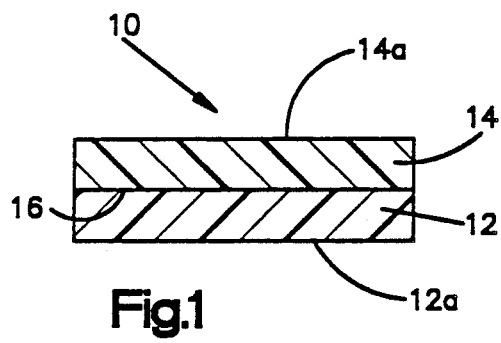
FIG. 1 is a fragmentary cross-sectional view showing a laminate having an integrally joined thermoplastic layer and thermoplastic elastomer layer in accordance with the invention.

Thermoplastic elastomers in accordance with the invention include multiblock copolymers of radial, triblock and diblock structures including non-rubbery segments of mono- and polycyclic aromatic hydrocarbons, and more particularly, mono- and polycyclic arenes. Illustrative mono- and polycyclic arenes include substituted and unsubstituted poly(vinyl)arenes of monocyclic and bicyclic structure. Preferred thermoplastic elastomers include non-rubbery segments of substituted or unsubstituted monocyclic arenes of sufficient segment molecular weight to assure phase separation at room temperature. Especially preferred monocyclic arenes comprise polystyrene and substituted polystyrenes including monomer units such as styrene and alkyl substituted styrene as illustrated by alpha methylstyrene and 4-methylstyrene. Preferred thermoplastic elastomers having non-rubbery segments of substituted or unsubstituted polycyclic arenes including monomer units such as 2-vinyl naphthalene and 6-ethyl-2-vinyl naphthalene.

The preferred elastomer rubbery segments are polymer blocks composed of homopolymers of a monomer or copolymers of two or more monomers selected from aliphatic conjugated diene compounds such as 1,3-butadiene and isoprene. Rubbery materials such as polyisoprene, polybutadiene and styrene butadiene rubbers may be used to form the elastomer rubbery segments. Particularly preferred rubbery segments include saturated olefin rubber of either ethylene/butylene or ethylene/propylene copolymers. These may be derived from the corresponding unsaturated polyalkylene moieties such as polybutadiene and polyisoprene by hydrogenation thereof.

In the preferred styrenic block copolymer systems, the rubbery segments may be saturated by hydrogenation of unsaturated precursors such as a styrene-butadiene-styrene (SBS) block copolymer having center or mid-segments comprising a mixture of 1,4 and 1,2 isomers. Upon hydrogenation of the latter, a styrene-ethylene-butylene-styrene (SEBS) block copolymer is obtained. Similarly, a styrene-isoprene-styrene (SIS) block copolymer precursor may be hydrogenated to yield a styrene-ethylene-propylene-styrene (SEPS) block copolymer.

Presently, the most preferred thermoplastic elastomers comprise SEBS block copolymers sold by the Shell Chemical Company under the designations KRATON G1650, G1652 and G1657. KRATON G1650 and G1652 are primarily of triblock structure and each has a styrene/rubber ratio of about 30/70. KRATON G1657 is a mixture of triblock and diblock structures in about a 70/30 ratio and has a styrene/rubber ratio of about 13/87.

The thermoplastic layer material may comprise a wide range of polymers, copolymers, interpolymers and blends thereof selected to meet the end use application. Illustrative thermoplastics which may be used alone or in blends include polyolefins such a polyethylene, polypropylene and polybutylene, thermoplastic polyesters, polyamides such as nylon, polysulfones, acrylic polymers such as polyethylene methyl polyacrylic acid, polyethylene ethyl acrylate and polyethylene methyl acrylate, polystyrene, polyurethanes, polycarbonates, halogenated polymers such as polyvinylchloride and polyvinylidene chloride, cellulosics, polyacrylonitriles, and ionomers based on sodium or zinc salts of ethylene/methacrylic acid.

The preferred thermoplastic layer materials comprise polyolefins including low, medium and high density polyethylene and, most preferably, polypropylene. Polyesters are also preferred to form the thermoplastic layer. However, the high polarity of certain polyesters may require the use of a tie coat to assure adherence to the thermoplastic elastomer. An example of a suitable tie coat material is a maleic anhydride functionalized triblock copolymer consisting of polystyrene end segments and poly(ethylene/butylene) mid-segments sold under the designation KRATON FG1901X by the Shell Chemical Company. Due to its functionality, KRATON FG1901X is adhesive with respect to many polar and non-polar thermoplastics.

Referring to FIG. 1, a laminate 10 of multilayer construction includes a thermoplastic carrier or base layer 12 integrally joined with a thermoplastic elastomer autoadhesive layer 14. The layers 12 and 14 are heat bonded or welded together along an interface 16 formed by the adjacent interior surfaces of the layers 12 and 14. Each of the layers 12 and 14 may range in thickness from about 0.1 mil to about 20 mils.

The layer 14 is formed of a suitable thermoplastic elastomer such as SEBS block copolymer. The exterior surface 14a of the elastomer 14 is autoadhesive in that it mutually adheres to like elastomer materials, but is otherwise substantially non-adhesive. The layer 12 is formed of polypropylene and includes exterior surface 12a which does not adhere to the surface 14a when they are pressed together at room temperature. Accordingly, the laminate 10 may be self-wound or stacked without a release liner. Embossing of the surface 12a further reduces the available contact surface and any tendency to adhere when the laminate 10 is self-wound or stacked.

The laminate 10 may be prepared by coextrusion processing using either feedblock or vane die apparatus commercially available, for example, as sold by The Cloren Company, Orange, Tex. The particular apparatus selected may depend upon the differences in processing temperatures and rheologies of the materials forming the layers. As a general guideline, degradation of a more sensitive coextruded polymer due to the higher processing temperatures of a less sensitive coextruded polymer is a function of both the temperature differential and exposure time. To that end, a vane die may be used to enhance thermal isolation by maintaining separation of coextruded polymers until they are joined in the preland of the die with a minimal contact time of the polymer melts. However, sufficient contact time is maintained to effect heat bonding or welding of the polymer layers and formation of an integral laminate. Herein, the coextrusion processing temperatures of SEBS polymer and polyolefin thermoplastic polymer are about 210° to about 220° C., and the rheological properties are sufficiently similar to allow the use of conventional coextrusion apparatus.

Figure 2:
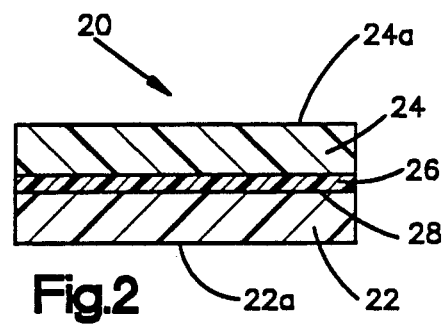
FIG. 2 is a view similar to FIG. 1 showing another embodiment of a laminate in accordance with the present invention having a tie layer joining a thermoplastic layer and a thermoplastic elastomer layer.

Referring to FIG. 2, a laminate 20 includes a polyester carrier or base layer 22 and an SEBS autoadhesive layer 24. The layer 24 includes an exterior surface 24a which provides autoadhesion properties and is substantially non-adhesive with respect to exterior surface 22a of the layer 22. Accordingly, the laminate 20 may also be self-wound or stacked without the use of a release liner.

The layers 22 and 24 are joined at an interface 26. In this instance, the polyester layer 22 is sufficiently polar to limit adhesion to the layer 24 without the use of a tie coat 28. The tie coat 28 may range up to about 5 mils in thickness, but it will ordinarily be only 0.1 to 2.0 mils thick. In the SEBS and polyester system of laminate 20, KRATON FG1901X forms a suitable heat bond with each of the adjacent layers 22 and 24 to enable an integral laminate.

The improved stability and anti-blocking properties of the thermoplastic elastomers in accordance with the invention are illustrated by the results reported in Table I below. In Table I, the variation with time of the strength of autoadhesively formed joints is compared for an SEBS elastomer laminate construction of the invention and an ethylene/propylene copolymer (EPR) laminate construction. The SEBS autoadhesive samples were prepared by coextrusion with polypropylene to form a carrier layer. In a similar manner, EPR samples were also prepared by coextrusion with polypropylene to form a carrier layer. Autoadhesion was measured using the T-peel test method set forth in ASTM D-1876-72. In accordance with this test method, the autoadhesive surfaces of 1" wide test samples are mutually adhered by similar rolling pressures. After dwell periods of 1 hour, 1 day and 13 days, the mutually adhered surfaces are separated by peeling at a rate of 10"/min. The peel test results reported in Table I below show that the elastomers of the invention including physical cross-links have more stable autoadhesive properties characterized by lower relative levels of mutual adherence. Following an extended dwell period during which increases in the initial autoadhesive strength occur, separating and rejoining the elastomer layers will reduce the autoadhesive strength to its original initial level.

TABLE I

| DWELL | MATERIAL | T-PEEL (N/M) |
| --- | --- | --- |
| 1 hour | SEBS/SEBS[1] | 526–788 |
| 1 day | SEBS/SEBS[1] | 526–788 |
| 13 days | SEBS/SEBS[1] | 876–1051 |
| 1 hour | EPR/EPR[2] | 613–876 |
| 1 day | EPR/EPR[2] | 701–1051 |
| 13 days | EPR/EPR[2] | 1051–1226 |

[1]KRATON G1657 by Shell Chemical Company. Typical styrene content 13%, tensile strength 3400 PSI and specific gravity of 0.91.
[2]VISTALON 719 by Exxon Chemical Company. Typical ethylene content of 75%, typical Mooney Viscosity of 54 ± 5 (ML 1 ± @ 127° C.) and specific gravity of 0.87.

The laminates of the invention are particularly useful in providing diaper tabs for disposable diapers since the strength of the autoadhesive bond following joint formation does not tend to increase during initial time intervals corresponding with or exceeding the duration of the end use application of such diaper tabs. As shown by the data of Table I, no significant increase in the degree of autoadhesion occurred for the SEBS test samples of the present invention during the initial one hour and one day time periods following fastening of the layers together to form an autoadhesive joint. The comparative EPR test samples resulted in substantial increases in autoadhesion during such initial time periods and attainment of absolute autoadhesion values which may be excessive in many short term applications requiring relatively low levels of autoadhesive strengths.

The autoadhesives of the present invention are also especially suited to diaper applications due to their non-contamination characteristics. More particularly, the non-adhesive properties of the thermoplastic elastomers eliminate contamination by many of the materials commonly present in such environments. For example, autoadhesion was not significantly reduced by chance contamination with small amounts of baby lotions and baby oils.

Figure 3:
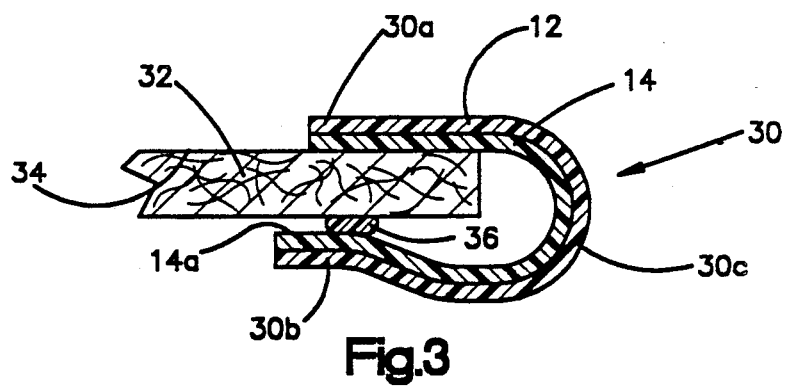
FIG. 3 is a fragmentary cross-sectional view showing a diaper fastener tab formed using the laminate of FIG. 1, the diaper fastener tab being shown applied to a disposable diaper and disposed in a storage position.

Referring to FIG. 3, a diaper fastening tab 30 incorporating laminate 10 of FIG. 1 as its principal component is shown. The laminate 10 may be sold in roll form to a diaper manufacturer for die cutting to form the tab 30. The tab 30 is secured in a storage position to a disposable diaper 32 of conventional construction. The diaper includes an outer liquid-impermeable layer comprising a plastic film 34 which may be formed of polyolefin or other suitable plastic.

The tab 30 has an elongate shape including opposed terminal segments 30a and 30b connected by an intermediate segment 30c. The autoadhesive layer 14 adjacent the segment 30a is permanently attached to the film 34 adjacent an outside corner of the diaper 32. The interface between the layer 14 and the film 34 is formed as a factory-joint by heat bonding or use of an adhesive with or without a tie coat since the layer 14 is otherwise substantially non-adhesive with respect to the film 34.

The tab 30 is mounted in the storage position by temporarily securing it at terminal segment 30b to a dollop 36 of autoadhesive elastomer. The dollop 36 may be of the same elastomeric composition as the layer 14 or a similar composition which is autoadhesive therewith. The dollop 36 is secured to the film 34 using a factory-joint as described above. Instead of dollop 36, a small piece of laminate 10 may be used with a factory-joint being provided between the layer 12 thereof and the film 34.

As shown in FIG. 3, the terminal segment 30b of the tab 30 extends beyond the dollop 36 in the storage position to provide a finger lift. No release liner or protective tab is required along the finger lift portion of the segment 30b since the layer 14 is substantially non-adhesive and non-tacky so as to thereby reduce contamination and interference with the subsequent use of the tab 30 to close the diaper 32.

Figure 4:
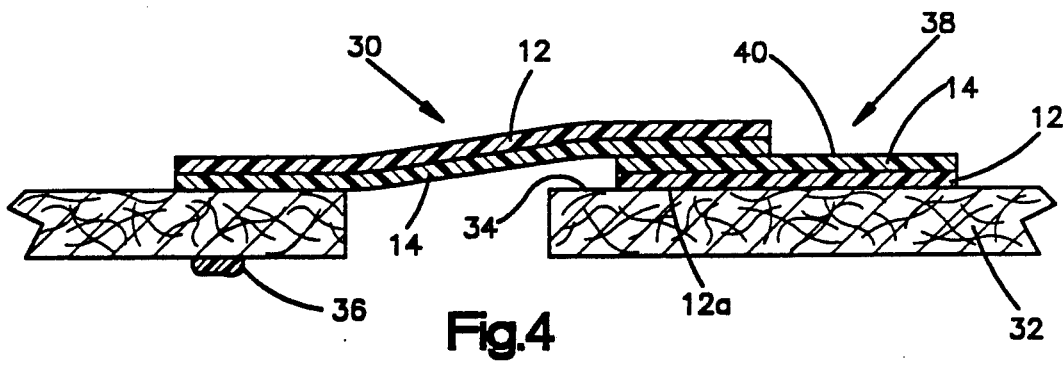
FIG. 4 is a fragmentary cross-sectional view showing the diaper fastener tab of FIG. 3 deployed to a diaper closure position releasably attached to a landing zone on another part of the diaper, the landing zone also being formed using the laminate of FIG. 1.

For purposes of diaper closure, a reinforcing tape 38 including a landing zone 40 is provided as shown in FIG. 4. The tape 38 is also formed using the laminate 10 of FIG. 1. More particularly, the surface 14a of the autoadhesive layer 14 provides the landing zone 40 and the thermoplastic layer 12, adhered to the film 34 at a factory-joint, provides reinforcement. This reinforcement facilitates closure and opening of the diaper 32 by fastening and rejoining the tab 30 adjacent the terminal segment 30b thereof to the landing zone 40.

A single piece of reinforcing tape 38 and landing zone 40 may be positioned along the front waist portion of the diaper 32 for cooperation with diaper tabs affixed to opposed diaper corners to fit the diaper in a closed condition to an infant or user. This is typically done by positioning the reinforcing tape 38 and landing zone 40 across the front waist portion of the diaper as opposed to the use of a separate piece of reinforcing tape for each of the diaper fastening tabs. In either such arrangement, it should be appreciated that the elimination of pressure-sensitive adhesives at the user-joints substantially reduces or eliminates the prior art contamination problems in such diaper constructions.

It should also be appreciated that since the physical cross-links of the elastomer are labile and reversible, the scrap materials resulting during production of the laminates can be recycled. Similarly, selection of recyclable carrier or base layers for use in the laminates themselves, permit the laminate products to be recycled.

It should be evident that this disclosure is by way of example and that various changes may be made by adding, modifying or eliminating details without departing from the fair scope of the teaching contained in this disclosure. The invention is therefore not limited to particular details of this disclosure except to the extent that the following claims are necessarily so limited.

We claim:

1. A diaper provided with tab fasteners for fastening the diaper in closed condition and with a reinforcing tape for receiving said fastening tabs, said reinforcing tape being bonded to the diaper proper by adhesive or other means, said tabs each being permanently bonded to the diaper proper at a factory-joint by adhesive or other means, and said tabs each being joinable to the reinforcing tape at a user-joint to close the diaper, said reinforcing tape and fastening tabs including autoadhesive surfaces for forming said user-joints, each of said autoadhesive surfaces being formed of thermoplastic elastomer which is substantially free of tackifier, said thermoplastic elastomer comprising a block copolymer of molecules having rubbery segments and thermodynamically incompatible non-rubbery segments which cooperate to form physical cross-links, said autoadhesive surfaces being substantially non-adhesive to reduce contamination thereof and to maintain their mutual adherence.

2. A diaper as set forth in claim 1, wherein said thermoplastic elastomer is formed of at least one copolymer selected from the group consisting of styrene-butadiene-styrene, styrene-ethylene-butylene-styrene, styrene-isoprene-styrene, and styrene-ethylene-propylene-styrene.

3. A diaper as set forth in claim 1, wherein said non-rubbery segments are selected from the group consisting of substituted and unsubstituted vinyl arenes.

4. A diaper as set forth in claim 3, wherein said non-rubbery segments comprise polymer blocks of monomer units selected from the group consisting of styrene, alpha methylstyrene, 4-methylstyrene, naphthalene, 2-vinyl naphthalene and 6-ethyl-2-vinyl naphthalene.

5. A diaper as set forth in claim 1, wherein said fastening tab and said reinforcing tape each comprise a multi-layer laminate including a layer of said thermoplastic elastomer which provides said autoadhesive surface.

6. A diaper as set forth in claim 5, wherein said laminate is a coextrudate including a base layer having said elastomeric layer thermally bonded to said base layer during coextrusion.

7. A diaper as set forth in claim 6, wherein said base layer of said reinforcing tape is bonded to said diaper at said factory-joint and said elastomeric layer of said fastening tab is bonded to said diaper at said factory-joint.

8. A diaper as set forth in claim 7, wherein said base layer is formed of thermoplastic material.

9. A method for manufacturing adhesively-tabbed diapers having reinforcing tapes for receiving fastening tabs to thereby fasten the diaper in closed condition comprising the steps of selecting for the exposed surfaces of the fastening tabs and reinforcing tapes a polymeric material which is an autoadhesive and non-tacky, said autoadhesive comprising a thermoplastic elastomer which is substantially free of tackifier, said thermoplastic elastomer comprising a block copolymer of molecules having rubbery segments and thermodynamically incompatible non-rubbery segments which cooperate to form physical cross-links, applying lengths of the reinforcing tape to diapers and also applying said fastening tabs to the diapers, said reinforcing tape being a coextrudate laminate including a base layer having said elastomeric layer thermally bonded to said base layer during coextrusion, whereby end users may achieve a good bond of said tabs to said reinforcing tape by non-pressure-sensitive adhesive means, and contamination of the fastening surfaces of the fastening tabs is avoided due to their non-tacky and non-pressure-sensitive adhesive nature.

10. A method as set forth in claim 9, wherein said thermoplastic elastomer is formed of at least one copolymer selected from the group consisting of styrene-butadiene-styrene, styrene-ethylene-butylene-styrene, styrene-isoprene-styrene, and styrene-ethylene-propylene-styrene.

* * * * *

UNITED STATES PATENT AND TRADEMARK OFFICE
CERTIFICATE OF CORRECTION

PATENT NO. : 5,085,655

DATED : February 4, 1992

INVENTOR(S) : Roger H. Mann et al.

It is certified that error appears in the above-identified patent and that said Letters Patent is hereby corrected as shown below:

On the Cover Page, Section [75], the second inventor's name should read --Karl Josephy--.

Signed and Sealed this

Eighteenth Day of May, 1993

Attest:

MICHAEL K. KIRK

*Attesting Officer*    *Acting Commissioner of Patents and Trademarks*